(12) United States Patent
Okada et al.

(10) Patent No.: US 11,653,837 B2
(45) Date of Patent: May 23, 2023

(54) OPTICAL OUTPUT MONITORING DEVICE, OPTICAL OUTPUT MONITORING METHOD, PROTECTIVE CAP, AND ADAPTER

(71) Applicant: HAMAMATSU PHOTONICS K.K., Hamamatsu (JP)

(72) Inventors: Hiroyuki Okada, Hamamatsu (JP); Tsuyoshi Kosugi, Hamamatsu (JP); Yoshiyuki Shimizu, Hamamatsu (JP); Yohei Takata, Hamamatsu (JP)

(73) Assignee: HAMAMATSU PHOTONICS K.K., Hamamatsu (JP)

( * ) Notice: Subject to any disclaimer, the term of this patent is extended or adjusted under 35 U.S.C. 154(b) by 893 days.

(21) Appl. No.: 16/314,877

(22) PCT Filed: Jun. 27, 2017

(86) PCT No.: PCT/JP2017/023576
§ 371 (c)(1),
(2) Date: Jan. 3, 2019

(87) PCT Pub. No.: WO2018/012280
PCT Pub. Date: Jan. 18, 2018

(65) Prior Publication Data
US 2019/0307330 A1    Oct. 10, 2019

(30) Foreign Application Priority Data
Jul. 12, 2016  (JP) .............................. JP2016-137330

(51) Int. Cl.
*A61B 5/00* (2006.01)
*A61B 18/24* (2006.01)
*G02B 6/42* (2006.01)

(52) U.S. Cl.
CPC ............ *A61B 5/0084* (2013.01); *A61B 18/24* (2013.01); *G02B 6/42* (2013.01)

(58) Field of Classification Search
CPC ...... A61B 18/24; A61B 18/245; H04W 76/30
See application file for complete search history.

(56) References Cited

U.S. PATENT DOCUMENTS 3,858,577 A     1/1975  Bass et al.
3,923,371 A *  12/1975  Dalgleish ............. G02B 6/3809
                                                        385/59

(Continued)

FOREIGN PATENT DOCUMENTS

CN      1670557 A     9/2005
CN    200972522 Y    11/2007

(Continued)

OTHER PUBLICATIONS

JPH0647056A translation (Year: 1994).*
International Preliminary Report on Patentability dated Jan. 24, 2019 for PCT/JP2017/023576.

*Primary Examiner* — Oommen Jacob
(74) *Attorney, Agent, or Firm* — Faegre Drinker Biddle & Reath LLP (57) ABSTRACT

A light output monitoring apparatus includes a light receiving unit, an attachment unit, an adapter, and a protective cap, and monitors a power of light output from a light emitting end of a catheter incorporating an optical fiber. The protective cap includes an insertion opening into which a part of the catheter of a predetermined range on the light emitting end side is removably inserted, includes a window portion for transmitting the light output from the light emitting end of the catheter, and is fixed in position by being inserted into a through-hole of the adapter. The adapter is fixed in position by being attached to the attachment unit.

4 Claims, 8 Drawing Sheets

(56) References Cited

U.S. PATENT DOCUMENTS

| | | | | |
|---|---|---|---|---|
| 4,321,057 A | * | 3/1982 | Buckles | C12Q 1/00 436/805 |
| 4,650,327 A | * | 3/1987 | Ogi | G01N 21/4785 356/243.1 |
| 4,776,340 A | * | 10/1988 | Moran | A61B 5/1459 600/327 |
| 4,782,819 A | * | 11/1988 | Adair | A61B 1/00128 606/10 |
| 4,823,167 A | * | 4/1989 | Manska | A61B 5/14552 356/243.1 |
| 5,115,126 A | * | 5/1992 | Ams | H04N 5/2256 356/73.1 |
| 5,293,438 A | * | 3/1994 | Konno | G02B 6/32 385/35 |
| 7,132,645 B2 | * | 11/2006 | Korn | A61B 5/02007 356/73.1 |
| 8,049,900 B2 | * | 11/2011 | Kemp | A61B 5/0073 356/497 |
| 8,133,167 B2 | * | 3/2012 | Gueye | A61N 5/1048 600/7 |
| 2004/0227056 A1 | * | 11/2004 | Neuberger | G01J 1/04 250/205 |
| 2008/0094631 A1 | | 4/2008 | Jung et al. | |
| 2008/0142815 A1 | * | 6/2008 | Morioka | G02B 6/4206 257/E33.076 |
| 2008/0275325 A1 | * | 11/2008 | Miyakawa | A61B 5/0071 600/368 |
| 2015/0272679 A1 | * | 10/2015 | Wang | A61B 18/24 606/15 |
| 2019/0307330 A1 | * | 10/2019 | Okada | A61B 5/0084 |

FOREIGN PATENT DOCUMENTS

| | | |
|---|---|---|
| JP | S60-16106 U | 2/1985 |
| JP | H2-140155 A | 5/1990 |
| JP | H3-014436 U | 2/1991 |
| JP | H6-047056 A | 2/1994 |
| JP | H06-47056 A | 2/1994 |
| JP | H06-042182 Y2 | 11/1994 |
| JP | H08-262278 A | 10/1996 |
| JP | 2001-337251 A | 12/2001 |
| JP | 4409499 B2 | 2/2010 |

* cited by examiner

OPTICAL OUTPUT MONITORING DEVICE, OPTICAL OUTPUT MONITORING METHOD, PROTECTIVE CAP, AND ADAPTER

TECHNICAL FIELD

The present invention relates to an apparatus and a method for monitoring a power of light output from a light emitting end of a catheter incorporating an optical fiber, and also relates to a protective cap and an adapter which are used in the apparatus and the method.

BACKGROUND ART

A catheter incorporating an optical fiber is capable of outputting laser light from a light emitting end that is inserted into the body of a patient, and the laser light is applied to an affected area, to thereby perform a treatment or diagnosis. Such a catheter is used for, for example, thrombolytic treatment (see Patent Document 1). Since it is necessary to reliably apply the laser light output from the light emitting end of the catheter to an affected area, a power of the laser light output from the light emitting end of the catheter is checked in advance (see Patent Documents 2 and 3). In the light output monitoring, it is important to fix a position of the light emitting end of the catheter with respect to a light receiving unit which receives light output from the light emitting end of the catheter, so that the output light can be appropriately made incident on the light receiving unit.

CITATION LIST

Patent Literature

Patent Document 1: Japanese Patent Publication No. 4409499
Patent Document 2: Japanese Examined Utility Model Application Publication No. H6-42182
Patent Document 3: Japanese Patent Application Laid-Open Publication No. H8-262278

SUMMARY OF INVENTION

Technical Problem

A catheter is used by being inserted into a body, and thus it is necessary to sterilize the catheter at the time of inserting it into the body. However, in the light output monitoring in advance, when a cleanliness of a jig that is used to fix the position of the light emitting end of the catheter is low, fungi and the like adhere to the catheter in contact with the jig. When the catheter to which fungi and the like adhere is inserted into the body of a patient, the patient may be affected with an infectious disease or the like. It is necessary to perform light output monitoring in advance while maintaining the cleanliness of the catheter, however, it is not easy.

The present invention has been made to solve the above problem, and an object thereof is to provide a light output monitoring apparatus and a light output monitoring method which are capable of easily performing light output monitoring in advance while maintaining a cleanliness of a catheter. Further, another object of the present invention is to provide a protective cap and an adapter which are preferably used in the apparatus and the method.

Solution to Problem

A light output monitoring apparatus according to the present invention is an apparatus for monitoring a power of light output from a light emitting end of a catheter incorporating an optical fiber, and includes (1) a light receiving unit for receiving light output from the light emitting end of the catheter, (2) an attachment unit provided at a position opposite to the light receiving unit, (3) an adapter detachably attached to the attachment unit, fixed in position by being attached to the attachment unit, and including a through-hole, and (4) a protective cap including an insertion opening provided at a first end and into which a part of the catheter of a predetermined range on the light emitting end side is removably inserted, including a window portion provided at a second end and for transmitting the light output from the light emitting end of the catheter, removably inserted into the through-hole of the adapter from the second end side, and fixed in position by being inserted into the through-hole. Further, in the light output monitoring apparatus, in a state where the adapter is fixed in position by being attached to the attachment unit, the part of the catheter of the predetermined range on the light emitting end side is inserted into the insertion opening of the protective cap, and the protective cap is fixed in position by being inserted into the through-hole of the adapter, an output light power is monitored by causing the light output from the light emitting end of the catheter to pass through the window portion of the protective cap and to be incident on the light receiving unit.

A light output monitoring method according to the present invention is a method for monitoring a power of light output from a light emitting end of a catheter incorporating an optical fiber, and uses the light receiving unit, the attachment unit, the adapter, and the protective cap described above, and the method includes fixing the adapter in position by being attached to the attachment unit, inserting the part of the sterilized catheter of the predetermined range on the light emitting end side into the insertion opening of the sterilized protective cap, and fixing the protective cap in position by being inserted into the through-hole of the adapter, and monitoring an output light power by causing the light output from the light emitting end of the catheter to pass through the window portion of the protective cap and to be incident on the light receiving unit.

A protective cap according to the present invention is a protective cap used, in an apparatus for monitoring a power of light output from a light emitting end of a catheter incorporating an optical fiber, for monitoring an output light power with a light receiving unit for receiving light output from the light emitting end of the catheter, an attachment unit provided at a position opposite to the light receiving unit, and an adapter detachably attached to the attachment unit, fixed in position by being attached to the attachment unit, and including a through-hole, and the protective cap includes an insertion opening provided at a first end and into which a part of the catheter of a predetermined range on the light emitting end side is removably inserted, and includes a window portion provided at a second end and for transmitting the light output from the light emitting end of the catheter, and is removably inserted into the through-hole of the adapter from the second end side, and is fixed in position by being inserted into the through-hole.

An adapter according to the present invention is an adapter used, in an apparatus for monitoring a power of light output from a light emitting end of a catheter incorporating an optical fiber, for monitoring an output light power with a light receiving unit for receiving light output from the light emitting end of the catheter, an attachment unit provided at a position opposite to the light receiving unit, and a protective cap including an insertion opening provided at a first end and into which a part of the catheter of a predetermined range on the light emitting end side is removably inserted, and including a window portion provided at a second end and for transmitting the light output from the light emitting end of the catheter, and the adapter is detachably attached to the attachment unit, and is fixed in position by being attached to the attachment unit, and includes a through-hole into which the protective cap is removably inserted from the second end side, and fixes the protective cap in position by being inserted into the through-hole.

Advantageous Effects of Invention

According to the present invention, it is possible to easily perform light output monitoring in advance while maintaining a cleanliness of a catheter.

DESCRIPTION OF EMBODIMENTS

Hereinafter, embodiments for carrying out the present invention will be described in detail with reference to the accompanying drawings. In the description of the drawings, the same elements will be denoted by the same reference signs, without redundant description. Further, the present invention is not limited to these examples.

Figure 1:
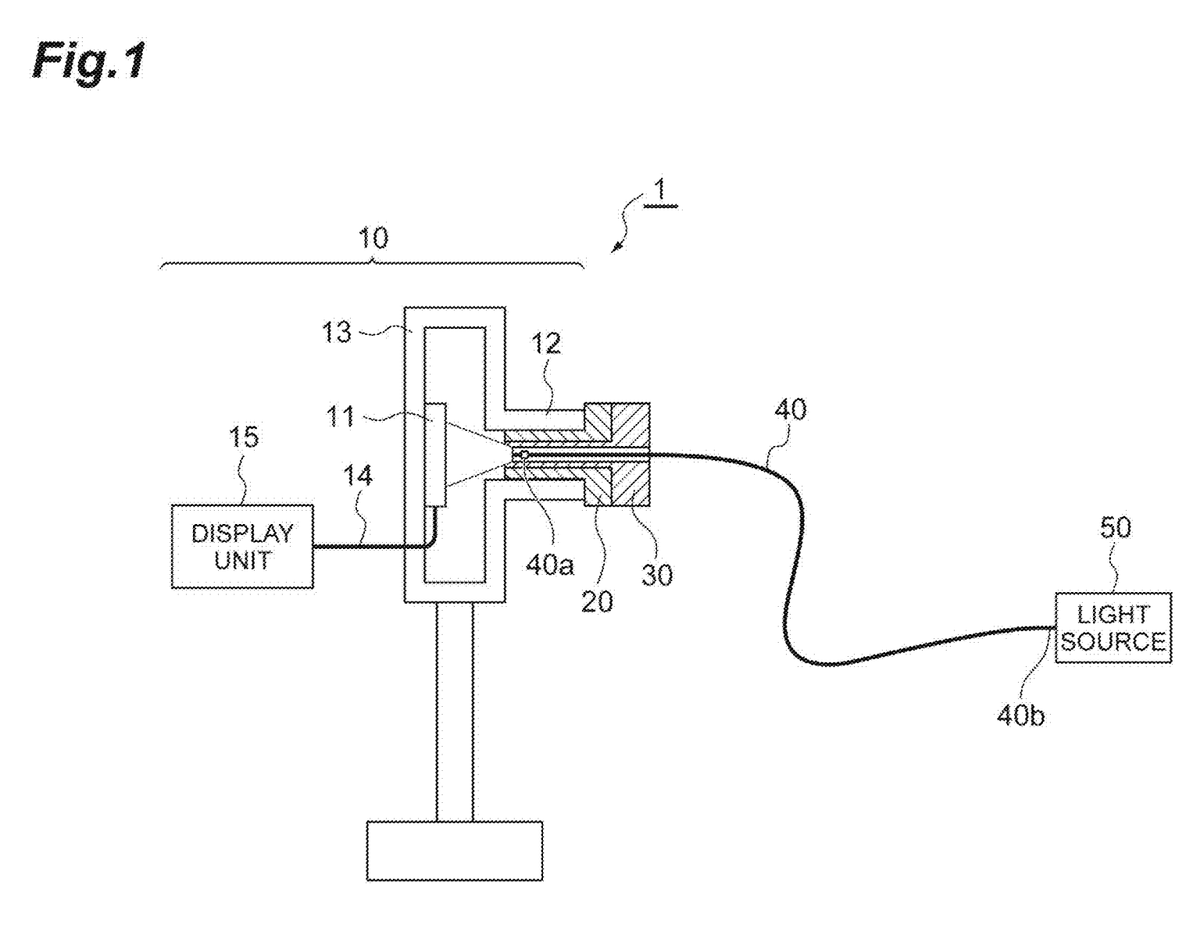
FIG. 1 is a diagram illustrating a configuration of a light output monitoring apparatus 1 according to the present embodiment.
Figure 2:
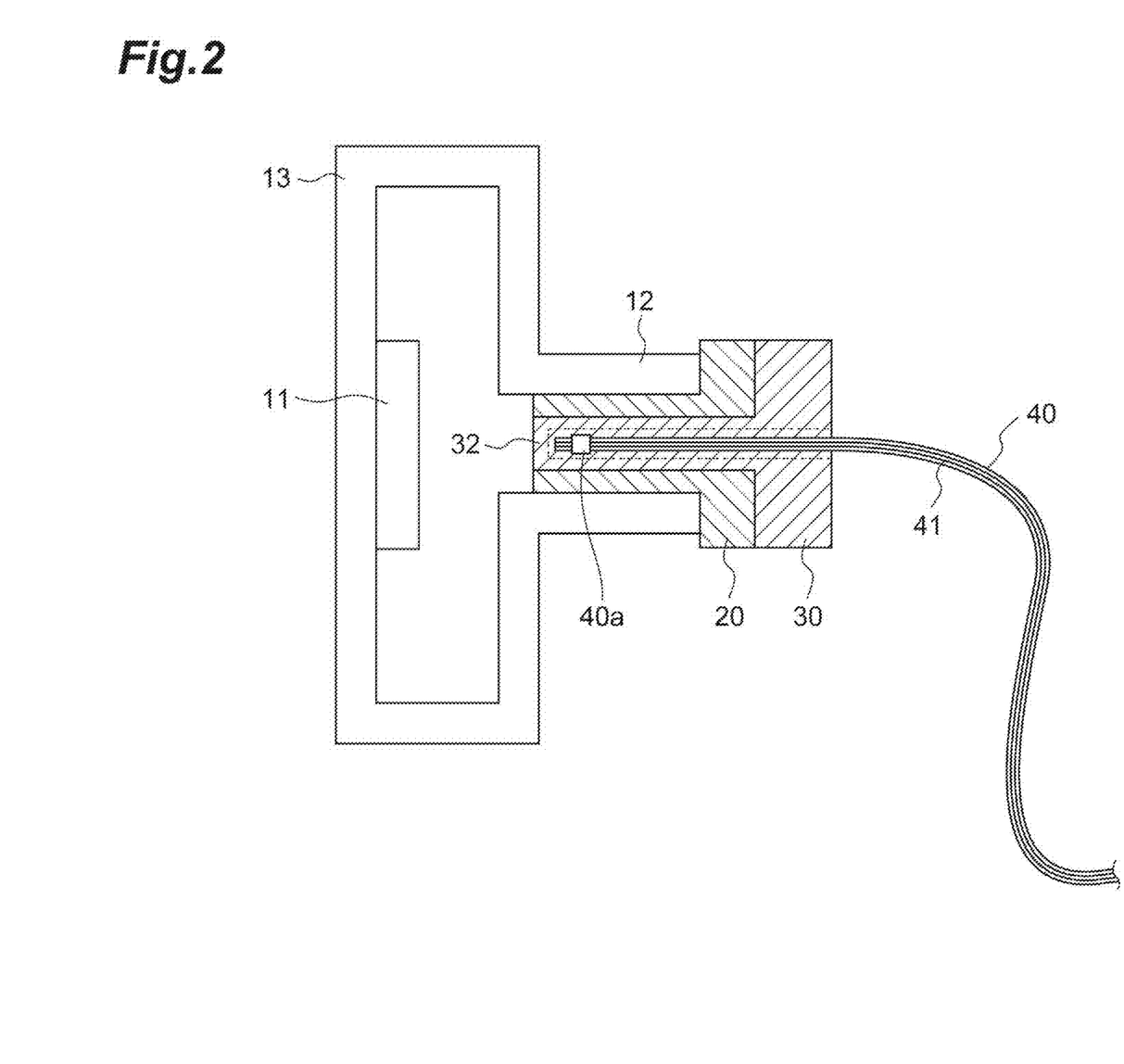
FIG. 2 is a diagram illustrating a configuration of a main part of the light output monitoring apparatus 1 according to the present embodiment.

FIG. 1 is a diagram illustrating a configuration of a light output monitoring apparatus 1 according to the present embodiment. FIG. 2 is a diagram illustrating a configuration of a main part of the light output monitoring apparatus 1 according to the present embodiment. The light output monitoring apparatus 1 includes a power meter 10, an adapter 20, and a protective cap 30, and is capable of monitoring a power of light output from a light emitting end 40a of a catheter 40 incorporating an optical fiber 41.

The power meter 10 includes a light receiving unit 11, an attachment unit 12, a housing 13, a signal cable 14, and a display unit 15. The light receiving unit 11 receives the light (preferably laser light) output from the light emitting end 40a of the catheter 40. The light receiving unit 11 includes, for example, a light absorber, converts absorbed light into heat, and outputs a change of the heat as a change of an electric signal. Examples of the light absorber include 3A-P manufactured by Ophir. The attachment unit 12 is provided at a position opposite to the light receiving unit 11, and includes an opening. The adapter 20 and the protective cap 30 are attached to the attachment unit 12. The laser light emitted from the light emitting end 40a of the catheter 40 inserted into the protective cap 30 is received by the light receiving unit 11.

The housing 13 holds the light receiving unit 11 and the attachment unit 12 while maintaining a relative positional relationship between the units. A part of the housing 13 may constitute the attachment unit 12. To prevent stray light from entering the light receiving unit 11, the housing 13 is preferably made of an opaque material, and preferably forms a closed space with the adapter 20 and the protective cap 30. The light receiving unit 11 is disposed in the closed space. The signal cable 14 sends an electric signal from the light receiving unit 11 to the display unit 15. The display unit 15 obtains the power of the light received by the light receiving unit 11 based on the electric signal, and displays the value of the light power.

The adapter 20 is detachable and attachable to the attachment unit 12, and is fixed in position by being attached to the attachment unit 12. Further, the adapter 20 includes a through-hole. The protective cap 30 is removable and insertable into the through-hole of the adapter 20, and is fixed in position by being inserted into the through-hole. The catheter 40 serving as an inspection object incorporates the optical fiber 41, causes the laser light output from a light source 50 to be incident on a light incident end 40b, and guides the laser light through the optical fiber 41 and emits the light from the light emitting end 40a.

Figure 3:
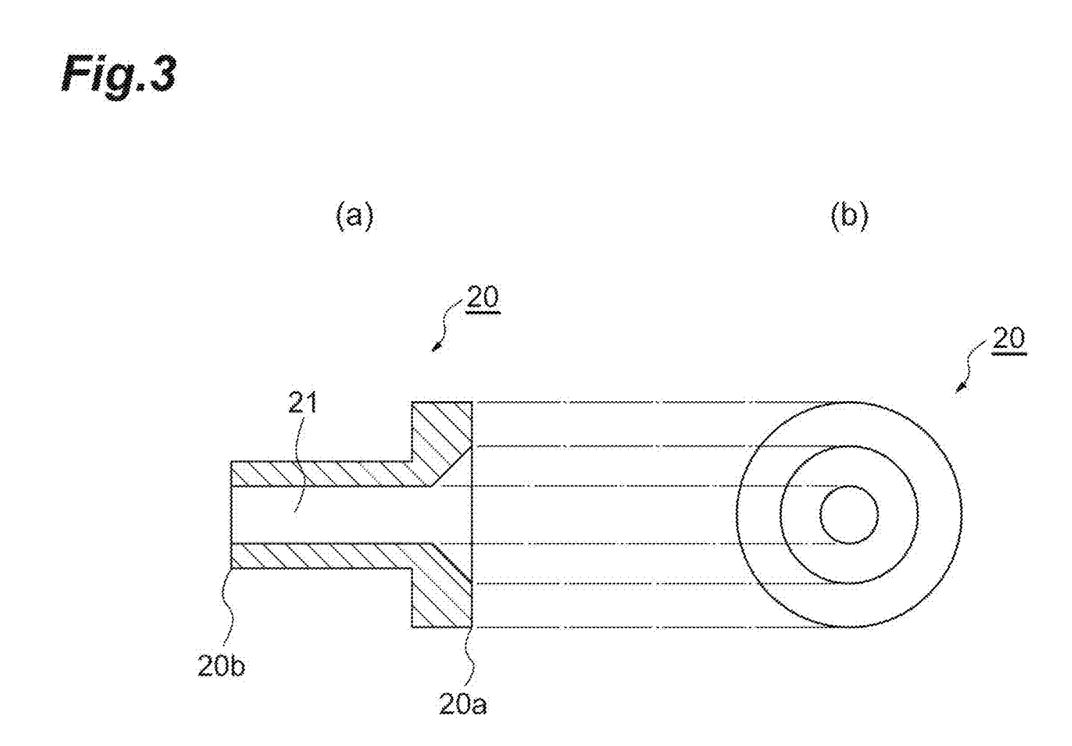
FIG. 3 includes (a), (b) diagrams illustrating a configuration of an adapter 20 according to the present embodiment.

FIG. 3 includes diagrams illustrating a configuration of the adapter 20 according to the present embodiment. (a) in FIG. 3 is a sectional view, and (b) in FIG. 3 is a side view. The schematic outer shape of the adapter 20 is rotationally symmetric about a central axis extending between a first end 20a and a second end 20b. The diameter of a predetermined range on the second end 20b side of the adapter 20 is smaller than the diameter on the first end 20a side, and an external thread is formed on the outer peripheral surface. An internal thread is formed on the inner peripheral surface of the circular opening of the attachment unit 12, and this screw enables the adapter 20 to be detachably attached to the attachment unit 12, and to be fixed in position by being attached to the attachment unit 12.

The adapter 20 includes a through-hole 21 extending between the first end 20a and the second end 20b. The protective cap 30 is inserted into the through-hole 21. To facilitate the insertion, a hole cross-sectional area preferably increases toward the end near the first end 20a (end at which the protective cap 30 is inserted) of the adapter 20. As a material for the adapter 20, for example, polyacetal is used.

Figure 4:
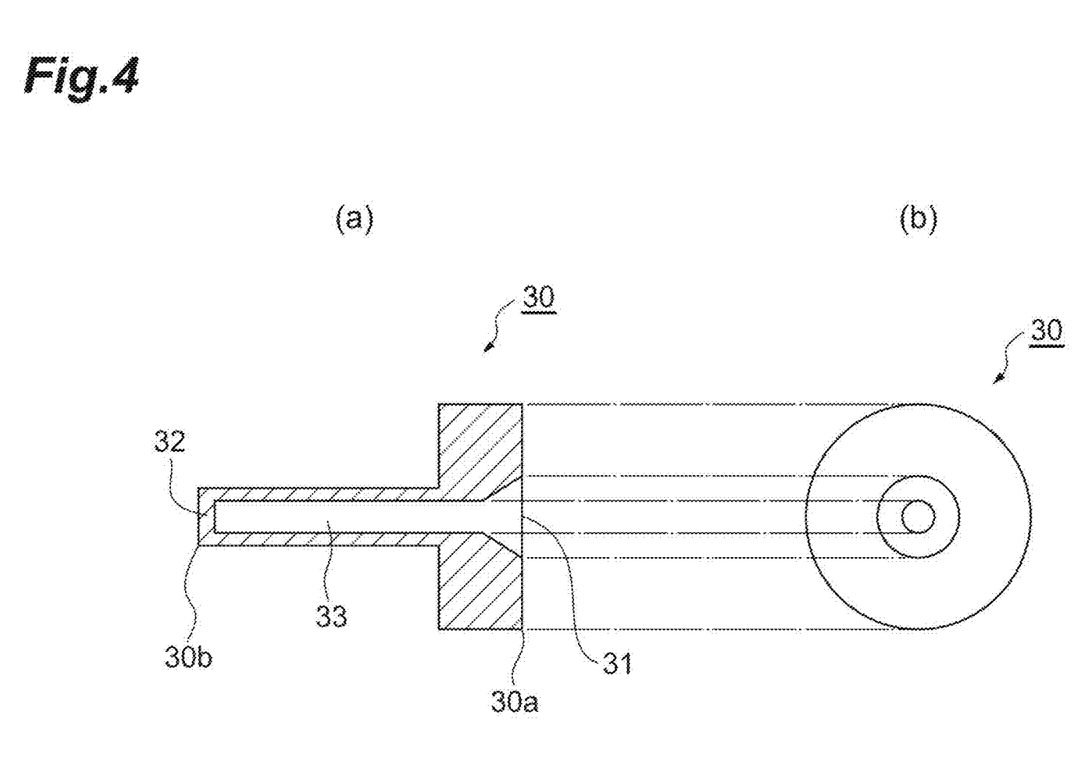
FIG. 4 includes (a), (b) diagrams illustrating a configuration of a protective cap 30 according to the present embodiment.

FIG. 4 includes diagrams illustrating a configuration of the protective cap 30 according to the present embodiment. (a) in FIG. 4 is a sectional view, and (b) in FIG. 4 is a side view. The schematic outer shape of the protective cap 30 is rotationally symmetric about a central axis extending between a first end 30a and a second end 30b. The diameter of a predetermined range on the second end 30b side of the protective cap 30 is smaller than the diameter on the first end 30a side. The protective cap 30 is removable and insertable into the through-hole 21 of the adapter 20 from the second end 30b side, and the small diameter portion is inserted into the through-hole 21 and fixed in position.

The protective cap 30 includes an insertion opening 31 which is provided at the first end 30a and into which a part of the catheter 40 of a predetermined range on the light emitting end 40a side is removably inserted, and includes a window portion 32 which is provided at the second end 30b and transmits laser light output from the light emitting end 40a of the catheter 40. The protective cap 30 has a hole 33 which is formed from the insertion opening 31 to the window portion 32 and enables the insertion of the catheter 40 of the predetermined range on the light emitting end 40a side. The hole 33 may have any diameter as long as the hole is large enough to prevent the catheter 40 having flexibility from being curved or bent. To facilitate the insertion of the catheter 40 from the insertion opening 31 to the hole 33, a hole cross-sectional area preferably increases toward the end near the first end 30a of the protective cap 30.

The material of the window portion 32 of the protective cap 30 is required to have high transparency for the light output from the light emitting end 40a of the catheter 40, and a material different from the material of the portion other than the window portion may be used. For example, acrylic is used as the material of the window portion 32 of the protective cap 30, and polyacetal is used as the material of the other portion.

In the measurement, the adapter 20 is attached to the attachment unit 12 with the screw and is fixed in position, the catheter 40 is inserted into the hole 33 from the insertion opening 31 of the protective cap 30 and is fixed in position by bringing the light emitting end 40a of the catheter 40 into contact with the window portion 32, and the protective cap 30 is inserted into the through-hole 21 of the adapter 20 and is fixed in position. In this state, a portion near the light emitting end 40a of the catheter 40 is perpendicular to a light receiving plane of the light receiving unit 11, and the laser light output from the light emitting end 40a is transmitted through the window portion 32 and is efficiently received by the light receiving unit 11.

The laser light output from the light emitting end 40a of the catheter 40 may be slightly absorbed when the light passes through the window portion 32. When the amount of light absorbed when the light passes through the window portion 32 is small, the display value of the power meter 10 may be adopted without change. The display value of the power meter 10 may be corrected in consideration of absorption characteristics of the light passing through the window portion 32.

Figure 5:
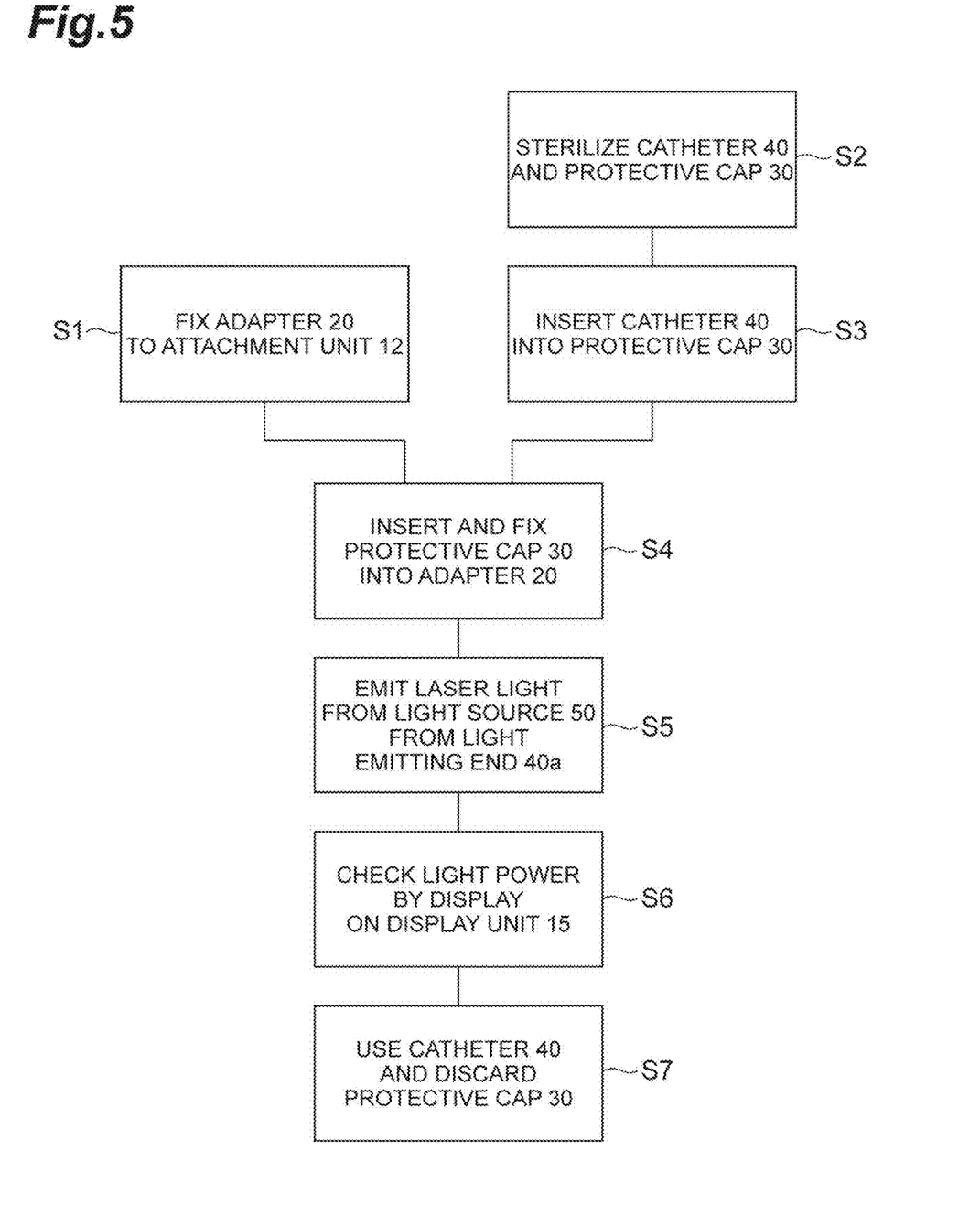
FIG. 5 is a flowchart illustrating a light output monitoring method according to the present embodiment.

Next, a method for monitoring a power of light output from the light emitting end of the catheter 40 by using the light output monitoring apparatus 1 according to the present embodiment will be described. FIG. 5 is a flowchart illustrating a light output monitoring method according to the present embodiment.

In step S1, the adapter 20 is attached to the attachment unit 12 and fixed in position. In step S2, the catheter 40 and the protective cap 30 are sterilized. In step S3, a part of the sterilized catheter 40 of the predetermined range of the light emitting end 40a side is inserted into the insertion opening 31 of the sterilized protective cap 30. At this time, the light emitting end 40a of the catheter 40 is brought into contact with the window portion 32 and fixed in position. In step S4, the protective cap 30 is inserted into the through-hole 21 of the adapter 20 and fixed in position. Here, the catheter 40 and the protective cap 30 may be sterilized in the attached state. In the case of touching the catheter 40, a tool with high cleanliness, such as sterilized gloves or instrument, is used.

In step S5, laser light is output from the light source 50, and the laser light is guided by the optical fiber 41 and is emitted from the light emitting end 40a of the catheter 40. Thus, the light output from the light emitting end 40a of the catheter 40 is caused to pass through the window portion 32 of the protective cap 30 and to be incident on the light receiving unit 11, thereby making it possible to monitor the output light power. In step S6, based on the value of the light power displayed on the display unit 15, it is checked whether laser light with a predetermined power is emitted from the light emitting end 40a of the catheter 40. In step S7, the catheter 40 is removed from the protective cap 30, and the catheter 40 is inserted into the body of a patient, and then the laser light output from the light emitting end 40a is applied to an affected area, thereby performing a treatment or diagnosis. The used catheter 40 and the protective cap 30 are discarded.

In the present embodiment, a part of the catheter 40 in the predetermined range on the light emitting end 40a side is inserted into the insertion opening 31 of the protective cap 30, thereby performing light output monitoring in advance. The protective cap 30 prevents the catheter 40 from coming into contact with the adapter 20. Therefore, even when the cleanliness of the adapter 20 is low, it is possible to prevent adhesion of fungi and the like on the catheter 40. It is possible to easily perform light output monitoring in advance while maintaining the cleanliness of the catheter 40.

Figure 6:
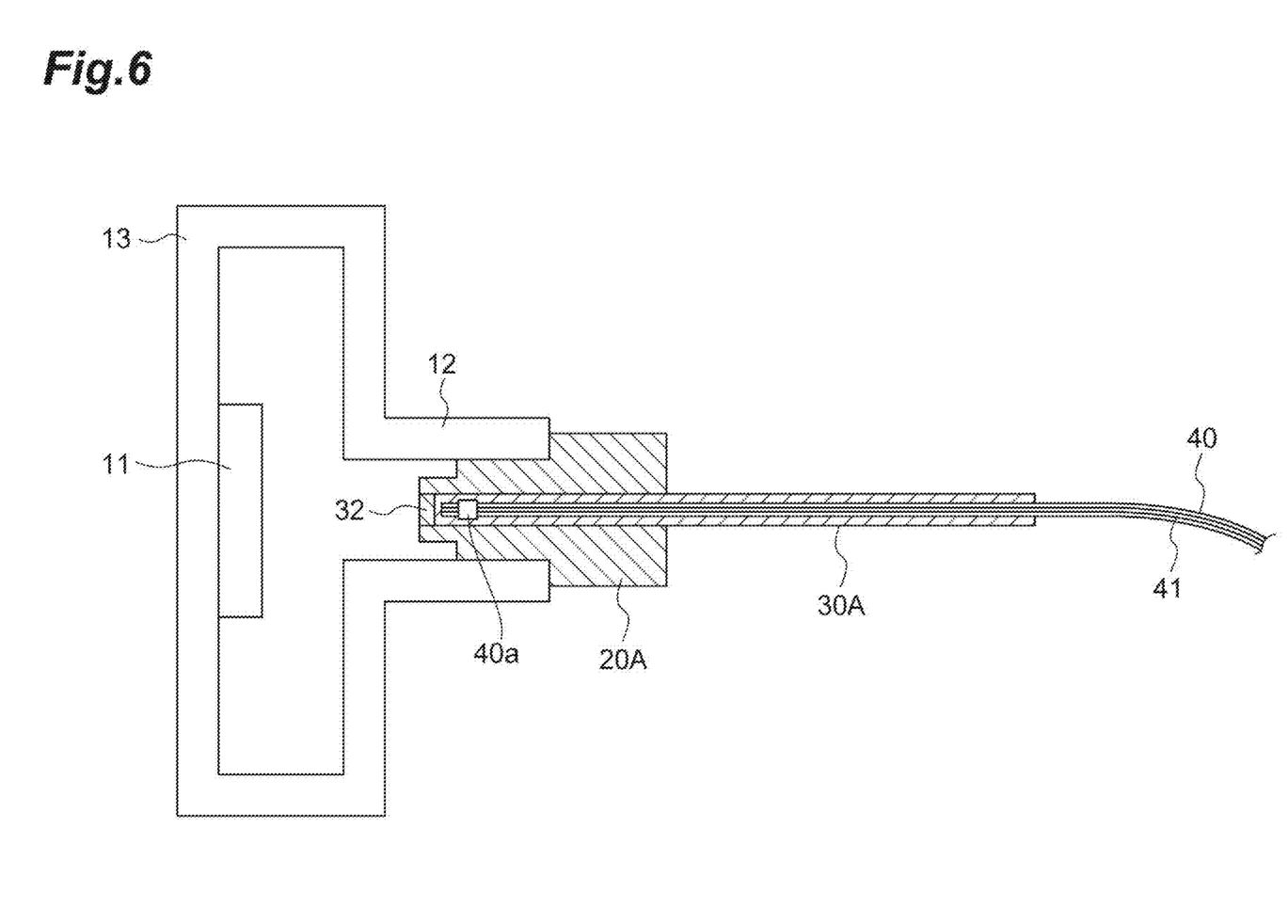
FIG. 6 is a diagram illustrating a configuration of a main part of a light output monitoring apparatus according to a modification.
Figure 7:
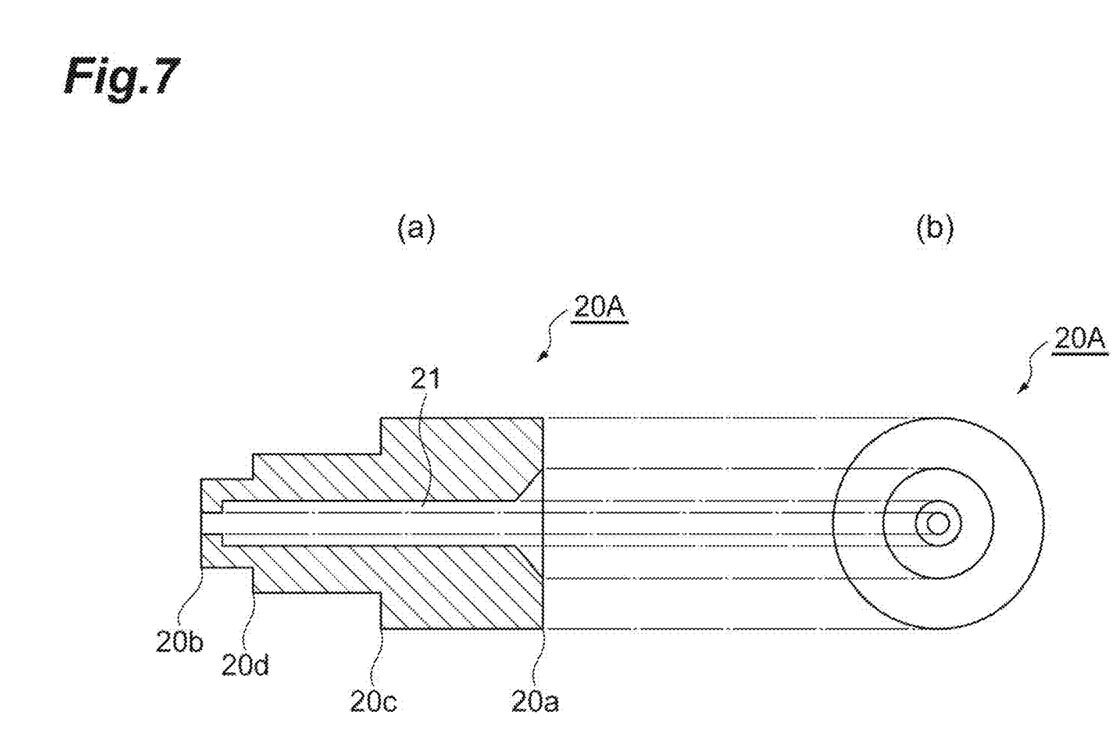
FIG. 7 includes (a), (b) diagrams illustrating a configuration of an adapter 20A according to the modification.
Figure 8:
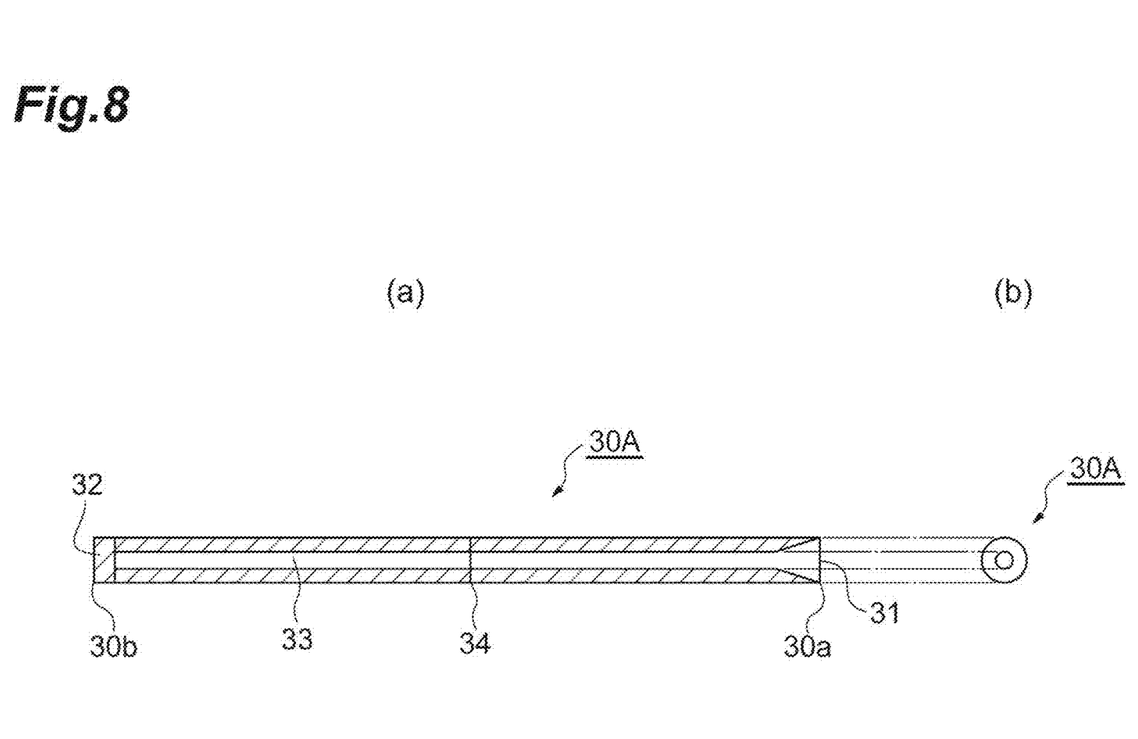
FIG. 8 includes (a), (b) diagrams illustrating a configuration of a protective cap 30A according to the modification.

The present invention is not limited to the embodiment described above, and can be modified in various ways. The adapter and the protective cap may have various shapes. For example, the shapes of an adapter 20A and a protective cap 30A as illustrated in FIG. 6 to FIG. 8 may be adopted. FIG. 6 is a diagram illustrating a configuration of a main part of a light output monitoring apparatus according to a modification. FIG. 7 includes diagrams illustrating a configuration of the adapter 20A according to the modification, (a) in FIG. 7 is a sectional view, and (b) in FIG. 7 is a side view. FIG. 8 includes diagrams illustrating a configuration of the protective cap 30A according to the modification, (a) in FIG. 8 is a sectional view, and (b) in FIG. 8 is a side view.

In the modification, the adapter 20A that is fixed in position by the attachment unit 12 provided at the position opposite to the light receiving unit 11 has an outer diameter larger than the opening diameter of the attachment unit 12 in a portion from the first end 20a to a position 20c, has an outer diameter corresponding to the opening diameter of the attachment unit 12 in a portion from the position 20c to a position 20d, and has an outer diameter smaller than the opening diameter of the attachment unit 12 in a portion from the position 20d to the second end 20b. On the outer peripheral surface of the portion from the position 20c to the position 20d of the adapter 20A, an external thread to be screwed with an internal thread formed on the inner peripheral surface of the circular opening of the attachment unit 12 is formed.

The outer diameter of the protective cap 30A is uniform between the first end 30a and the second end 30b. The opening diameter of the second end 20b of the adapter 20A is set to be smaller than the outer diameter of the protective cap 30A so that the second end 30b of the protective cap 30A can be brought into contact therewith. On the outer peripheral surface of the protective cap 30A, a mark 34 is formed or depicted at a position located at a predetermined distance from the second end 30b. The mark 34 may be formed with an outer diameter that partially varies. With this configuration, the range of the protective cap 30A inserted into the through-hole 21 of the adapter 20A can be appropriately set.

In addition, the outer shape and the hole shape of the section of each of the attachment unit, the adapter, and the protective cap are not limited to a circle, but instead may be other shapes. Any shape may be used as long as the attachment unit can fix the position of the adapter, the adapter can fix the position of the protective cap, and the protective cap can fix the position of the catheter.

The light output monitoring apparatus according to the above embodiment is an apparatus for monitoring a power of light output from a light emitting end of a catheter incorporating an optical fiber, and is configured to include (1) a light receiving unit for receiving light output from the light emitting end of the catheter, (2) an attachment unit provided at a position opposite to the light receiving unit, (3) an adapter detachably attached to the attachment unit, fixed in position by being attached to the attachment unit, and including a through-hole, and (4) a protective cap including an insertion opening provided at a first end and into which a part of the catheter of a predetermined range on the light emitting end side is removably inserted, including a window portion provided at a second end and for transmitting the light output from the light emitting end of the catheter, removably inserted into the through-hole of the adapter from the second end side, and fixed in position by being inserted into the through-hole. Further, in the light output monitoring apparatus, in a state where the adapter is fixed in position by being attached to the attachment unit, the part of the catheter of the predetermined range on the light emitting end side is inserted into the insertion opening of the protective cap, and the protective cap is fixed in position by being inserted into the through-hole of the adapter, an output light power is monitored by causing the light output from the light emitting end of the catheter to pass through the window portion of the protective cap and to be incident on the light receiving unit.

The light output monitoring method according to the above embodiment is a method for monitoring a power of light output from a light emitting end of a catheter incorporating an optical fiber, and uses the light receiving unit, the attachment unit, the adapter, and the protective cap described above, and is configured to include fixing the adapter in position by being attached to the attachment unit, inserting the part of the sterilized catheter of the predetermined range on the light emitting end side into the insertion opening of the sterilized protective cap, and fixing the protective cap in position by being inserted into the through-hole of the adapter, and monitoring an output light power by causing the light output from the light emitting end of the catheter to pass through the window portion of the protective cap and to be incident on the light receiving unit.

The protective cap according to the above embodiment is a protective cap used, in an apparatus for monitoring a power of light output from a light emitting end of a catheter incorporating an optical fiber, for monitoring an output light power with a light receiving unit for receiving light output from the light emitting end of the catheter, an attachment unit provided at a position opposite to the light receiving unit, and an adapter detachably attached to the attachment unit, fixed in position by being attached to the attachment unit, and including a through-hole, and the protective cap includes an insertion opening provided at a first end and into which a part of the catheter of a predetermined range on the light emitting end side is removably inserted, and includes a window portion provided at a second end and for transmitting the light output from the light emitting end of the catheter, and is removably inserted into the through-hole of the adapter from the second end side, and is fixed in position by being inserted into the through-hole.

Further, in the protective cap of the above configuration, a hole cross-sectional area may increase toward the end near the first end.

The adapter according to the above embodiment is an adapter used, in an apparatus for monitoring a power of light output from a light emitting end of a catheter incorporating an optical fiber, for monitoring an output light power with a light receiving unit for receiving light output from the light emitting end of the catheter, an attachment unit provided at a position opposite to the light receiving unit, and a protective cap including an insertion opening provided at a first end and into which a part of the catheter of a predetermined range on the light emitting end side is removably inserted, and including a window portion provided at a second end and for transmitting the light output from the light emitting end of the catheter, and the adapter is detachably attached to the attachment unit, and is fixed in position by being attached to the attachment unit, and includes a through-hole into which the protective cap is removably inserted from the second end side, and fixes the protective cap in position by being inserted into the through-hole.

Further, in the adapter of the above configuration, a hole cross-sectional area may increase toward the end near the end from which the protective cap is inserted.

INDUSTRIAL APPLICABILITY

The present invention can be utilized as a light output monitoring apparatus and a light output monitoring method which are capable of easily performing light output monitoring in advance while maintaining a cleanliness of a catheter, and as a protective cap and an adapter which are preferably used in the apparatus and the method.

REFERENCE SIGNS LIST

1—light output monitoring apparatus, 10—power meter, 11—light receiving unit, 12—attachment unit, 13—housing, 14—signal cable, 15—display unit, 20—adapter, 21—through-hole, 30—protective cap, 31—insertion opening, 32—window portion, 33—hole, 34—mark, 40—catheter, 40a—light emitting end, 41—optical fiber, 50—light source.

The invention claimed is:

1. A light output monitoring apparatus for monitoring a power of light output from a light emitting end of a catheter incorporating an optical fiber, the apparatus comprising:
   a light receiving unit configured to receive light output from the light emitting end of the catheter;
   an attachment unit provided at a position opposite to the light receiving unit;
   an adapter detachably attached to the attachment unit, fixed in position by being attached to the attachment unit, and including a through-hole; and
   a protective cap including an insertion opening provided at a first end and into which a part of the catheter of a predetermined range on the light emitting end side is removably inserted, including a window portion provided at a second end and configured to transmit the light output from the light emitting end of the catheter, removably inserted into the through-hole of the adapter from the second end side, and the protective cap being fixed in position to the adapter by being inserted into the through-hole, wherein
   in a state where the adapter is fixed in position by being attached to the attachment unit, the part of the catheter of the predetermined range on the light emitting end side is inserted into the insertion opening of the protective cap, the catheter is removably fixed in position to the protective cap by bringing the light emitting end of the catheter into contact with the window portion of the protective cap, and the protective cap is fixed in position by being inserted into the through-hole of the adapter, an output light power is monitored by causing the light output from the light emitting end of the catheter to pass through the window portion of the protective cap and to be incident on the light receiving unit, and after monitoring the output light power, the catheter is removed from the protective cap.

2. A light output monitoring method for monitoring a power of light output from a light emitting end of a catheter incorporating an optical fiber, the method using:

a light receiving unit configured to receive light output from the light emitting end of the catheter;

an attachment unit provided at a position opposite to the light receiving unit;

an adapter detachably attached to the attachment unit, fixed in position by being attached to the attachment unit, and including a through-hole; and a protective cap including an insertion opening provided at a first end and into which a part of the catheter of a predetermined range on the light emitting end side is removably inserted, including a window portion provided at a second end and configured to transmit the light output from the light emitting end of the catheter, removably inserted into the through-hole of the adapter from the second end side, and the protective cap being fixed in position to the adapter by being inserted into the through-hole, the method comprising:

fixing the adapter in position by being attached to the attachment unit;

inserting the part of the sterilized catheter of the predetermined range on the light emitting end side into the insertion opening of the sterilized protective cap, removably fixing the catheter in position to the protective cap by bringing the light emitting end of the catheter into contact with the window portion of the protective cap, and fixing the protective cap in position by being inserted into the through-hole of the adapter;

monitoring an output light power by causing the light output from the light emitting end of the catheter to pass through the window portion of the protective cap and to be incident on the light receiving unit; and removing the catheter from the protective cap after monitoring the output light power.

3. The light output monitoring apparatus according to claim 1, wherein in the protective cap, a hole cross-sectional area increases toward the end near the first end.

4. The light output monitoring apparatus according to claim 1, wherein in the adapter, a hole cross-sectional area increases toward the end near the end from which the protective cap is inserted.

* * * * *